(12) United States Patent
Navok et al.

(10) Patent No.: US 8,568,300 B2
(45) Date of Patent: Oct. 29, 2013

(54) HERMETIC ENDOSCOPE ASSEMBLAGE

(75) Inventors: Ezra Navok, Stamford, CT (US);
Christopher A. Cook, New York, NY (US)

(73) Assignee: GYRUS ACMI, Inc., Southborough, MA (US)

( * ) Notice: Subject to any disclaimer, the term of this patent is extended or adjusted under 35 U.S.C. 154(b) by 1401 days.

(21) Appl. No.: 12/167,901

(22) Filed: Jul. 3, 2008

(65) Prior Publication Data

US 2008/0300463 A1    Dec. 4, 2008

Related U.S. Application Data

(62) Division of application No. 11/300,068, filed on Dec. 13, 2005, now Pat. No. 7,410,462.

(60) Provisional application No. 60/635,928, filed on Dec. 13, 2004.

(51) Int. Cl.
*A61B 1/00* (2006.01)
*A61B 1/04* (2006.01)

(52) U.S. Cl.
USPC .......................................................... 600/129

(58) Field of Classification Search
USPC .................................. 600/129, 133, 175, 176
See application file for complete search history.

(56) References Cited

U.S. PATENT DOCUMENTS

| | | |
|---|---|---|
| 3,126,625 A | 3/1964 | Laing |
| 4,669,471 A | 6/1987 | Hayashi |
| 4,878,485 A | 11/1989 | Adair |
| 4,905,670 A | 3/1990 | Adair |
| 4,911,148 A | 3/1990 | Sosnowski et al. |
| 5,083,549 A | 1/1992 | Cho et al. |
| RE33,854 E | 3/1992 | Adair |
| 5,137,013 A | 8/1992 | Chiba et al. |
| 5,163,950 A | 11/1992 | Pinchuk et al. |
| 5,188,094 A | 2/1993 | Adair |
| 5,199,417 A | 4/1993 | Muller et al. |
| 5,212,595 A | 5/1993 | Dennison, Jr. et al. |
| 5,349,137 A | 9/1994 | Cedrone |
| 5,396,880 A | 3/1995 | Kagan et al. |
| 5,599,278 A | 2/1997 | Hibbard |
| 5,810,713 A | 9/1998 | Rondeau et al. |
| 5,836,867 A | 11/1998 | Speier et al. |

(Continued)

FOREIGN PATENT DOCUMENTS

| | | |
|---|---|---|
| DE | AS1122738 | 1/1962 |
| DE | 20104874 | 8/2001 |

(Continued)

OTHER PUBLICATIONS

Office Action dated Mar. 1, 2011, and issued by the Patent Office of Japan in Japanese Patent Application No. 2008-107401; (in the Japanese language); 3 pages.

(Continued)

*Primary Examiner* — Philip R Smith
(74) *Attorney, Agent, or Firm* — The Dobrusin Law Firm, P.C.

(57) ABSTRACT

Hermetically sealed enclosures and constructions are disclosed for use in endoscopic systems, particularly endoscopic systems with electronic imaging and illumination systems in the enclosures. Compound optical windows are also disclosed for use in the systems. The compound optical windows may have separate panes for an imaging system and an illumination system, and contrast-reducing optical boundaries are between panes.

9 Claims, 6 Drawing Sheets

(56) References Cited

U.S. PATENT DOCUMENTS

| | | | |
|---|---|---|---|
| 6,030,339 | A | 2/2000 | Tatsuno et al. |
| 6,080,101 | A | 6/2000 | Tatsuno et al. |
| 6,146,326 | A | 11/2000 | Pollack et al. |
| 6,302,841 | B1 | 10/2001 | Hatori et al. |
| 6,328,691 | B1 | 12/2001 | Rudischhauser |
| 6,390,972 | B1 | 5/2002 | Speier et al. |
| 6,419,626 | B1 | 7/2002 | Yoon |
| 6,425,857 | B1 | 7/2002 | Rudischhauser et al. |
| 6,428,180 | B1 | 8/2002 | Karram et al. |
| 6,485,413 | B1 | 11/2002 | Boppart et al. |
| 6,514,197 | B1 | 2/2003 | Ouchi et al. |
| 6,547,721 | B1 | 4/2003 | Higuma et al. |
| 6,547,722 | B1 | 4/2003 | Higuma et al. |
| 6,558,316 | B2 | 5/2003 | Kikuchi et al. |
| 6,572,537 | B2 | 6/2003 | Futatsugi et al. |
| 6,641,530 | B2 | 11/2003 | Mitsumori |
| 6,692,431 | B2 | 2/2004 | Kazakevich |
| 6,716,161 | B2 | 4/2004 | Higuma et al. |
| 6,749,560 | B1 | 6/2004 | Konstorum et al. |
| 6,776,328 | B2 | 8/2004 | Rice et al. |
| 6,780,151 | B2 | 8/2004 | Grabover et al. |
| 6,805,664 | B2 | 10/2004 | Doyle et al. |
| 6,923,758 | B2 | 8/2005 | Ishibiki |
| 7,410,462 | B2 | 8/2008 | Navok |
| 7,448,994 | B2 | 11/2008 | Baholzer |
| 2001/0016679 | A1 | 8/2001 | Futatsugi et al. |
| 2002/0010385 | A1 | 1/2002 | Ishibiki |
| 2002/0128539 | A1 | 9/2002 | Higuma et al. |
| 2004/0176661 | A1 | 9/2004 | Futatsugi et al. |
| 2005/0267329 | A1 | 12/2005 | Konstorum |
| 2005/0267444 | A1 | 12/2005 | Griffin et al. |
| 2006/0222300 | A1 | 10/2006 | Frenzel et al. |

FOREIGN PATENT DOCUMENTS

| | | |
|---|---|---|
| DE | 10252446 | 5/2004 |
| DE | 10344768 | 8/2005 |
| GB | 906278 | 8/1960 |
| JP | 60-009591 | 1/1985 |
| JP | 61-002834 | 1/1986 |
| JP | 3-223707 | 10/1991 |
| JP | 04-335611 | 11/1992 |
| JP | 07-047050 | 2/1995 |
| JP | 07-093463 | 4/1995 |
| JP | 08-065579 | 3/1996 |
| JP | 08-136826 | 5/1996 |
| JP | 09-323174 | 12/1997 |
| JP | 10-262927 | 10/1998 |
| JP | 11-305146 | 11/1999 |
| JP | 2000-111777 | 4/2000 |
| JP | 2000-120997 | 4/2000 |
| JP | 2000-262458 | 9/2000 |
| JP | 2000-287913 | 10/2000 |
| JP | 2000-321394 | 11/2000 |
| JP | 2001078956 | 3/2001 |
| JP | 2001-212075 | 8/2001 |
| JP | 2003-289458 | 10/2003 |
| JP | 2004-081231 | 3/2004 |
| JP | 2005-70505 | 3/2005 |
| WO | WO9306767 | 4/1993 |
| WO | WO03098913 | 11/2003 |
| WO | WO2004036266 | 5/2004 |
| WO | WO2006066022 | 6/2006 |
| WO | WO2007113815 | 10/2007 |

OTHER PUBLICATIONS

Office Action dated Mar. 1, 2011, and issued by the Patent Office of Japan in Japanese Patent Application No. 2008-107400; (in the Japanese language); 3 pages.

Office Action dated Apr. 15, 2011, and issued by the United States Patent and Trademark Office in U.S. Appl. No. 11/842,811(in the Japanese language); 11 pages.

Office Action dated May 12, 2010, and issued by the German Patent and Trademark Office in German Patent Application No. 102008018932.4-35 (in the German language); 5 pages—English language translation of Office Action included—5 pages.

US 5,858,664, 2/1999, Speier et al. (withdrawn).

International Search Report and Written Opinion dated Jul. 26, 2007 for International Patent Application No. PCT/US2005/045469, filed Dec. 13, 2005.

Office Action dated Aug. 20, 2007 for parent U.S. Appl. No. 11/300,068, now granted U.S. Patent No. 7,410,462; 11 pages.

Final Office Action dated Mar. 11, 2008 for parent U.S. Appl. No. 11/300,068, now granted U.S. Patent No. 7,410,462; 14 pages.

Applicant response and amendment filed Nov. 9, 2007 for parent U.S. Appl. No. 11/300,068, now granted U.S. Patent No. 7,410,462; Response includes Exhibit A with Society of Manufacturing Engineers website; 25 pages.

Applicant substitute amendment filed Apr. 30, 2008 for parent U.S. Appl. No. 11/300,068, now granted U.S. Patent No. 7,410,462; 21 pages.

Office Action dated Jul. 29, 2011, for U.S. Appl. No. 11/842,811; 15 pages total.

German Examination Report dated Apr. 30, 2010 for related German patent application No. 11205002972.7; an informal English translation of the Report provided by the German agent is included; 8 pages total.

Japanese Office Action dated Feb. 16, 2010 for related Japanese patent application No. 2007-546902; an informal English summary of the Report provided by the Japanese agent is included; 5 pages total.

Office action from the Patent Office of Germany dated Feb. 2, 2010 for related German patent application No. 102008018922.7, including informal English translation, 8 pages total.

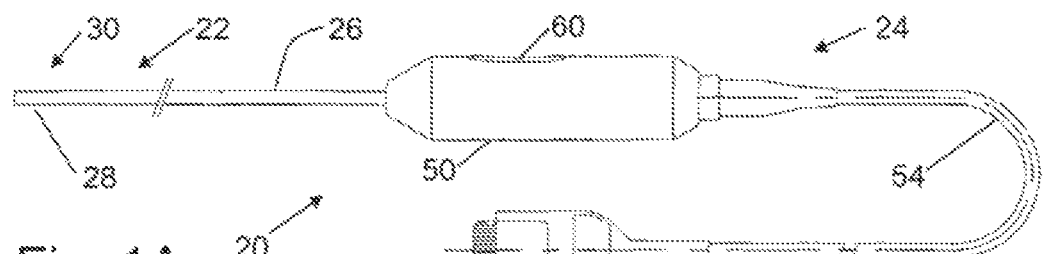
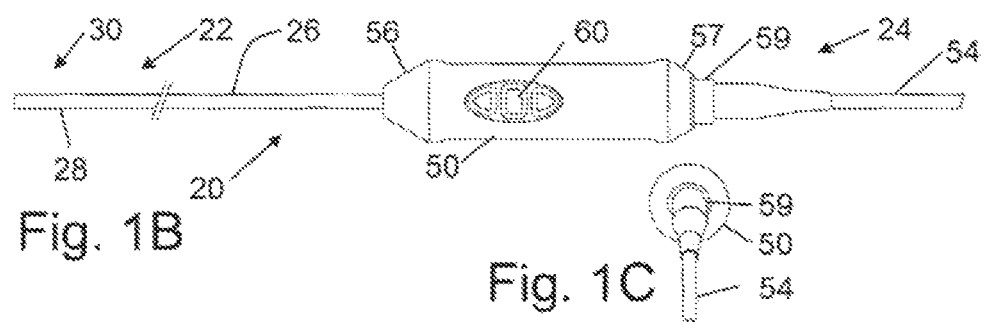
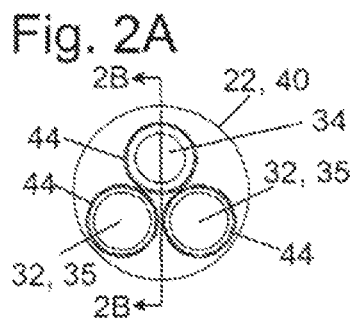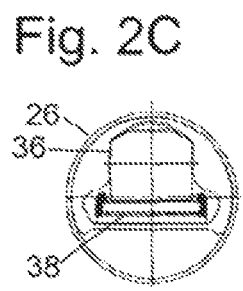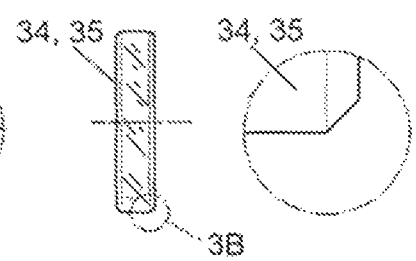
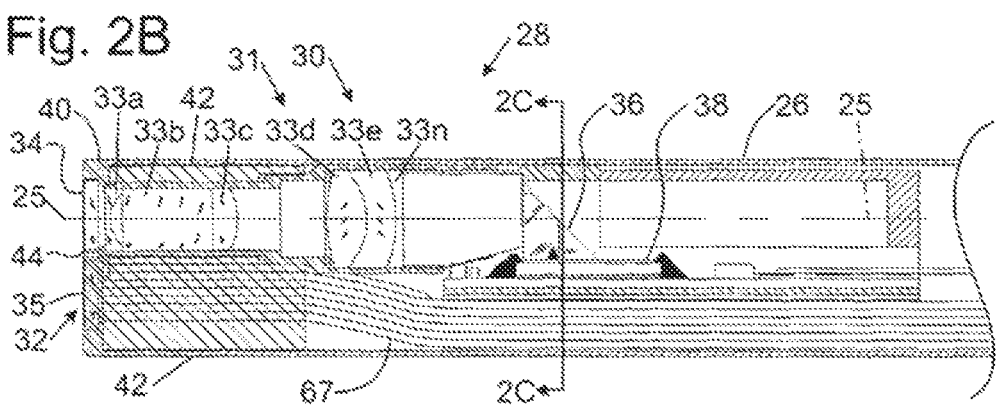

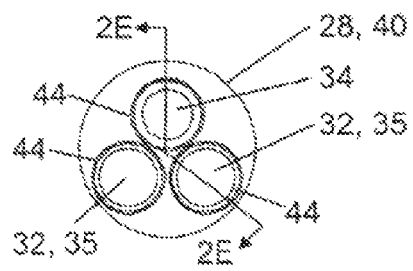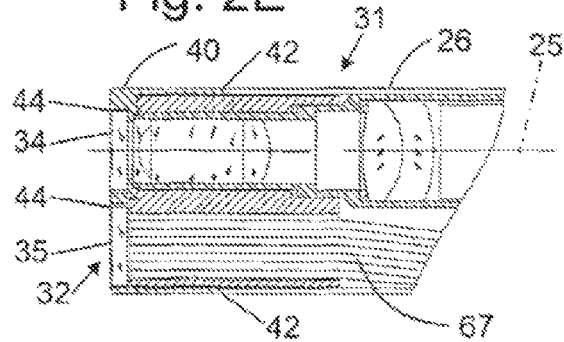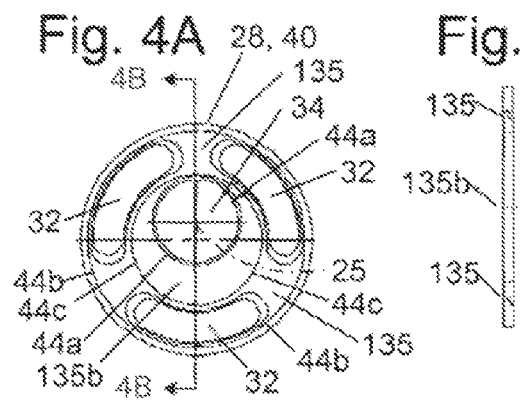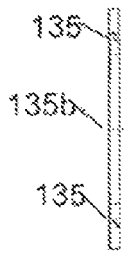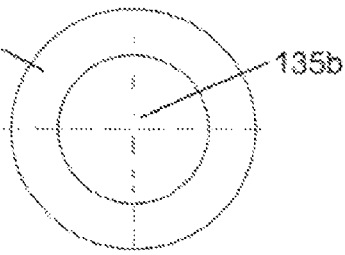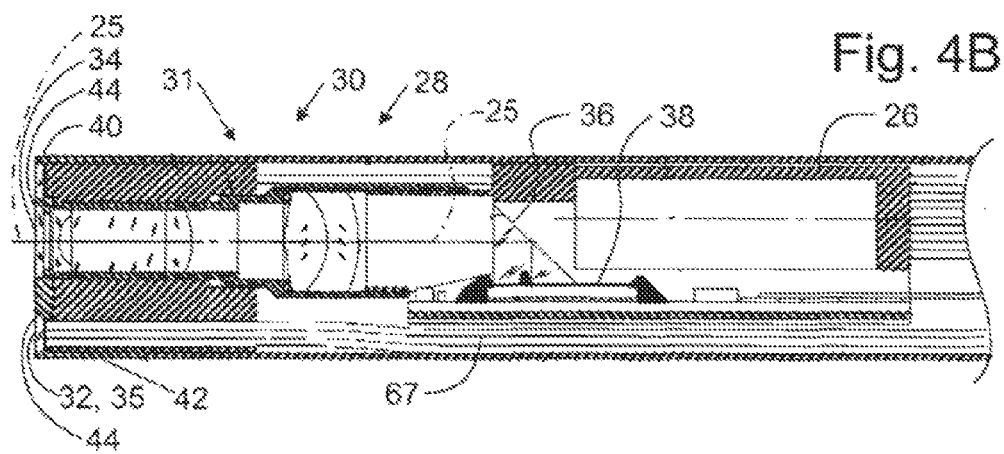

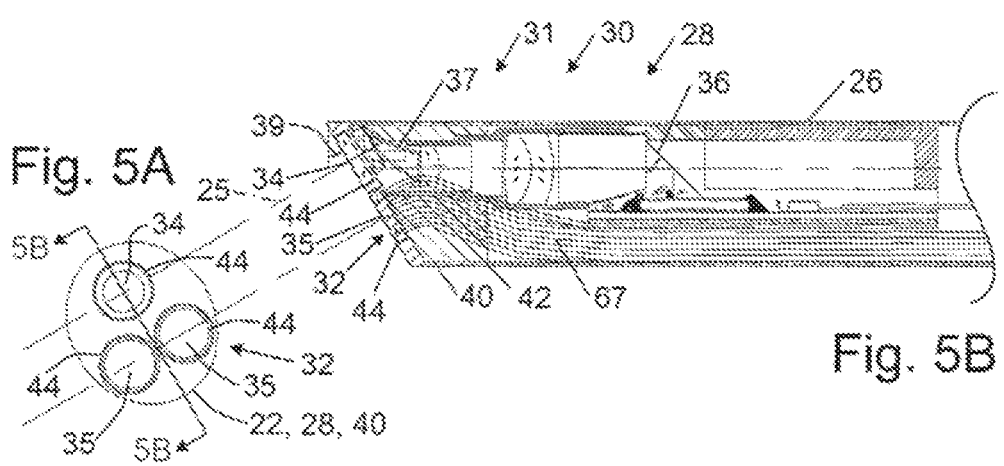
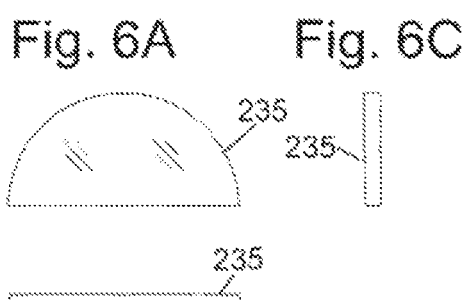
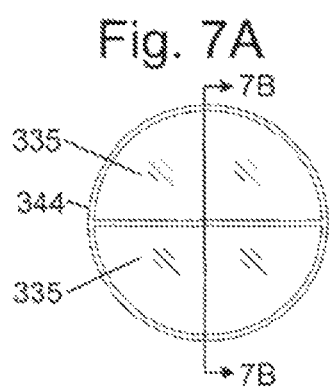
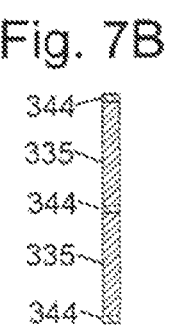
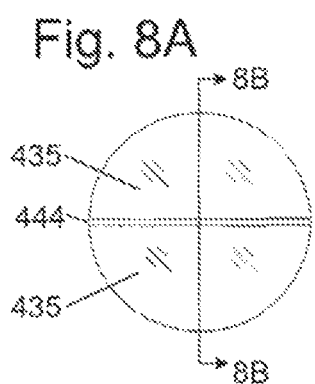
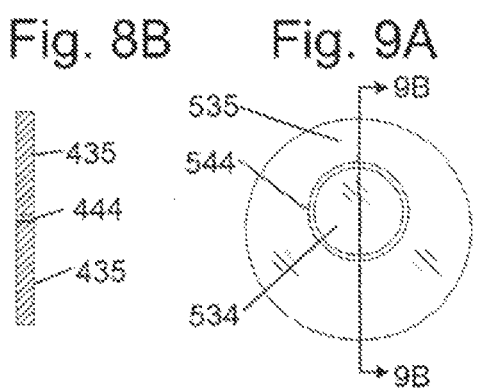
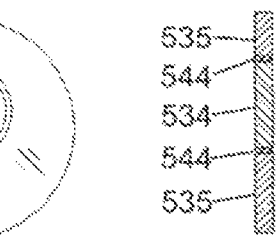

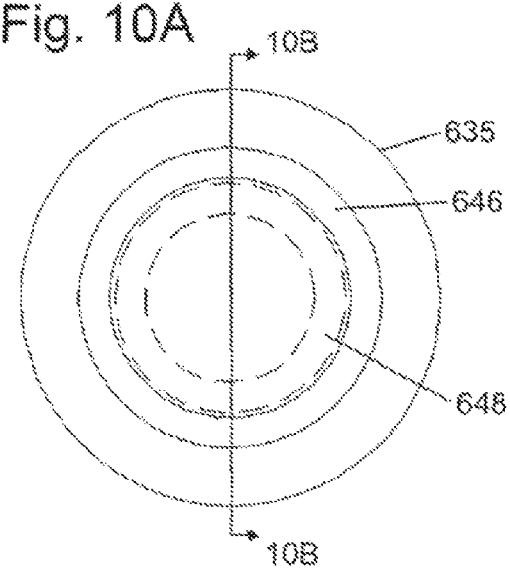
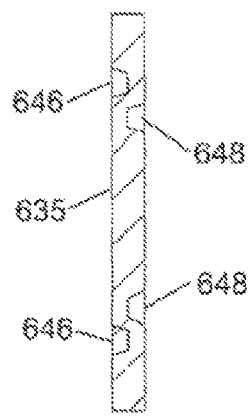
Fig. 10A  Fig. 10B
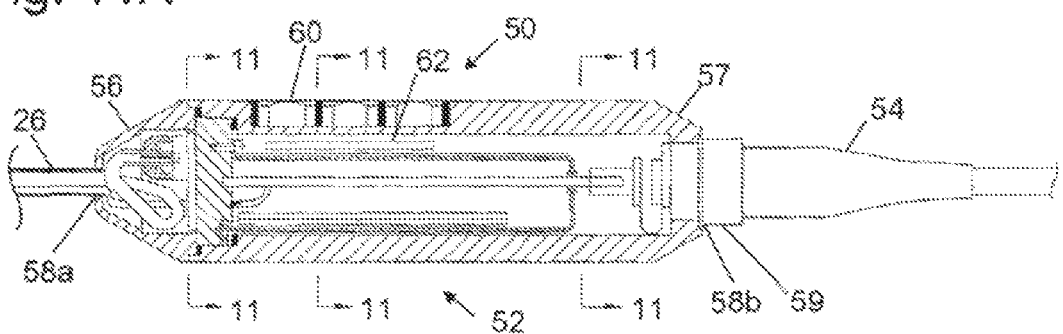
Fig. 11A
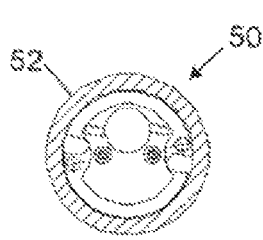
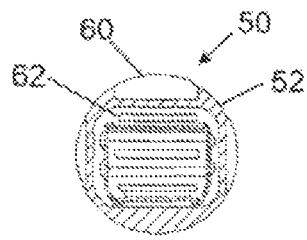
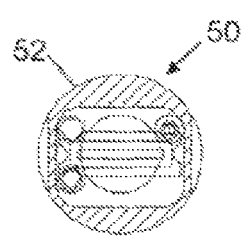
Fig. 11B  Fig. 11C  Fig. 11D

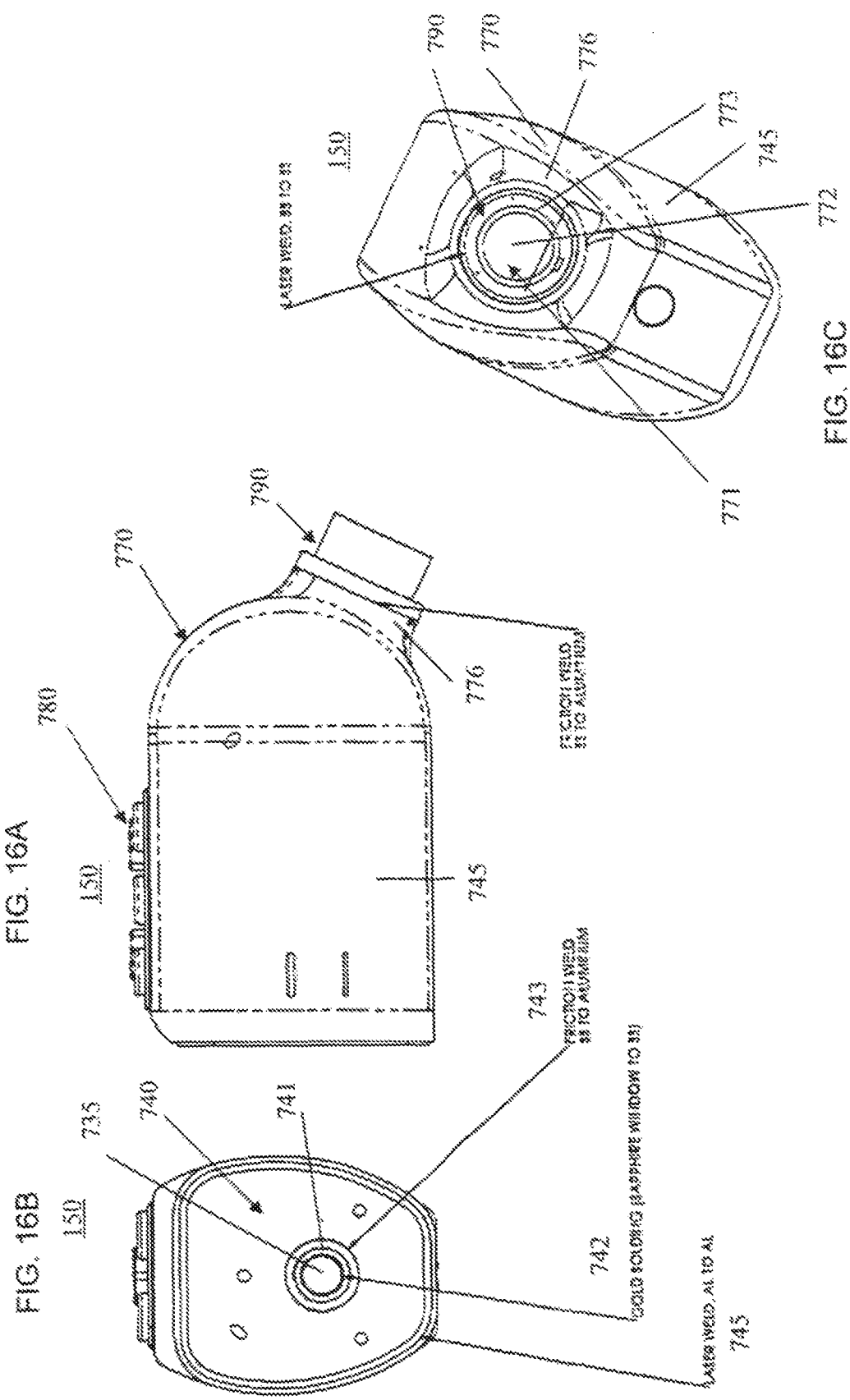

HERMETIC ENDOSCOPE ASSEMBLAGE

CROSS-REFERENCE TO RELATED APPLICATIONS

This application is a Divisional of, claiming priority to and the benefit of U.S. non-provisional patent application Ser. No. 11/300,068, filed Dec. 13, 2005, which claims priority to and the benefit of U.S. provisional patent application Ser. No. 60/635,928, filed on Dec. 13, 2004, by Ezra Navok, et al., entitled "ENDOSCOPE ASSEMBLAGE," the entire disclosure of which are hereby incorporated by reference as if set forth in their entirety for all purposes.

BACKGROUND

A medical endoscope is an instrument used to inspect the inside of a body. A typical endoscope has a distal end comprising an optical or electronic imaging system, a proximal end with controls for manipulating the tool and devices for viewing the image, and a solid or tubular elongate shaft connecting the ends. To use an endoscope, a physician inserts the distal end into a patient through a natural orifice or an artificial incision and then pushes the shaft into the patient until the distal end reaches a site of interest. The proximal end remains outside the patient and typically connects to an eyepiece, video monitor, or other equipment. Some endoscopes let the physician pass tools or treatments down a hollow channel, for example, to resect tissue or retrieve objects. Other endoscopes are strictly inspection devices and not used for remote procedures.

After an endoscope is used on a particular patient, the endoscope must be sterilized before it can be used again. The goal of sterilization is to remove all foreign matter and all pathogens. A traditional method for sterilizing metallic surgical instruments is to place them in a device called an autoclave. An autoclave is a strong, enclosed pressure vessel with a heater and a pressure-tight door. An autoclave heats its contents with pressurized steam to a high temperature, above the boiling point of water, killing pathogens and microorganisms.

The high temperature and pressure within an autoclave can damage or degrade endoscopes and similar instruments, however. As endoscopes have become more sophisticated and costly, it has become more important to reduce or prevent this damage and degradation while continuing to rely on an autoclave for positive sterilization.

A typical electronic endoscope may contain circuit boards, integrated circuits, conductors, connectors, lenses, prisms, image sensors, and so on. A typical endoscope protects these internal parts, for example, during sterilization, through a sealing system based on O-rings, silicone seals, epoxy seals, or similar flexible, semi-flexible, or adhesive sealants. Unfortunately, some of these sealing methods cannot withstand repeated exposure to pressurized steam in an autoclave or to other sterilization conditions. Sterilization procedures for endoscopes commonly start with partial or total disassembly followed by sterilization by immersion in sterilant gasses, liquids, or plasmas. These sterilization procedures are labor-intensive and expensive. Worse, they are not always totally effective at disinfecting and decontaminating the instrument. Disease-causing microorganisms may survive processing, creating a risk of iatrogenic infection to subsequent patients—a complication that contributes to extended hospital stays and increased mortality and morbidity.

What is needed is an electronic endoscope that can withstand rigorous sterilization in an autoclave—which, by necessity and design, creates a very harsh environment. Ideally, the endoscope would not require significant disassembly prior to autoclaving. Ideally, it would survive repeated autoclaving without damage or degradation. Some attempts have been made to provide hermetic enclosures. For example, U.S. Pat. No. 6,572,537 discloses an endoscope having a solid-state image pickup device with a distal tip sapphire window and a sapphire rear end cover. The cover and window are subjected to a metallization process and then joined by an airtight brazing process to metal members to form a hermetic seal. Soldered or brazed connections are used in various other places in the device to form hermetic seals. (See also U.S. Pat. Nos. 6,716,161; 6,547,722; 6,547,721; 6,425,857; 6,328,691; 6,146,326; 6,080,101; 6,030,339; 5,868,664; 5,810,713; 5,188,094; and 4,878,485). All the foregoing patents are hereby incorporated by reference, as if set forth herein in their entireties.

Unfortunately, the foregoing needs have not been met by the prior art because the mere design of a hermetic enclosure, which might be capable of withstanding harsh environmental conditions, does not automatically satisfy other functional and operational needs. In particular, different parts of an endoscope ideally require different material attributes. Some desirable materials that can withstand harsh conditions may not easily join to other desirable materials. This is certainly the case relative to, for example, aluminum, stainless steel, and titanium metals, or their alloys, each of which may provide desirable operational or functional attributes.

More specifically, the need to join dissimilar metals partly results from the part-by-part selection of materials guided by the purpose of each part and the properties of the available metals and alloys. The parts of medical instruments that actually enter a patient's body are often made from stainless steel, an FDA-approved material with corrosion-resistant properties desirable for maintaining a sterile surface. Stainless steel has poor heat conductivity and is relatively heavy, however. Aluminum, in contrast, has excellent heat conductivity, making it a preferred material for the parts of medical instruments that contain heat sources such as electrical or electronic devices. Aluminum is also lighter than stainless steel, making it better for large parts, especially those require that precise manipulation. Aluminum is unfortunately prone to oxidation, making it non-ideal for parts that pass into the body; and aluminum is relatively soft, making it non-ideal for parts exposed to friction, scratching, and wear. Titanium, on the other hand, is exceptionally strong, hard, and tough, making it preferential for parts exposed to friction and wear. As a result of its toughness, titanium traditionally has been difficult to machine, so that titanium parts have been expensive. Ongoing improvements in metalworking technologies have lead to an ongoing expansion of the use of titanium in medical instruments and elsewhere.

Producing a hermetic enclosure greatly benefits from the ability to form fused joints such as welds. Dissimilar metals such as stainless steel, aluminum, and titanium are difficult or impossible to weld to each other via laser welding, arc welding, and similar techniques, however. One approach would be to manufacture all structural components from compatible metals or alloys. For example, the structural parts of the objective head, shaft, and handle all might be made from stainless steel, facilitating the formation of fused joints. This approach precludes the part-by-part selection of metals and alloys, a considerable drawback. Fusing optical glasses used in objective heads presents similar challenges.

SUMMARY OF THE INVENTIVE CONCEPTS

In certain embodiments, the present inventive concept is directed to a hermetically sealed endoscope, as well as related methods, with the following qualities, alone or in combination:

In certain embodiments, the present inventive concepts are directed to a hermetically sealed enclosure, suitable for use in an electronic endoscope, with an onboard image sensor such as a CCD or CMOS chip, capable of repeated sterilization cycles in an autoclave. To survive repeated autoclaving without major disassembly, an endoscope enclosure protects all joints, controls, and connections with melted-metal or coalesced-metal sealing techniques, such as soldering, brazing, laser welding, or friction welding. It may also use melted glass plugs through which electrical leads may pass from the interior of an enclosure to the exterior. It does not need to employ exposed O-ring seals, silicone seals, epoxy seals, or similar flexible, semi-flexible, or adhesive seals.

Certain embodiments of the present inventive concept protect all internal parts of the imaging system, including the optical system, the illumination system, or both by using ports or windows made from nonmetallic, optical materials, such as, optical sapphire, that are soldered into an aperture provided in a cap-like cover that is subsequently welded to the endoscope shaft. The assembly by melted-metal seals creates a hermetically sealed objective head that protects the optical and illumination systems. Pre-soldering the windows and ports into the cover, and subsequently welding the cover to the shaft, advantageously eliminates heat damage during assembly to both optical and illumination components. Illumination components such as fiber-optic bundles and LEDs are particularly heat sensitive, an attribute that might otherwise force the use of an epoxy seal (for example) between the light port and cover. Pre-soldering the light port into the cover eliminates this non-durable, non-hermetic seal, so that not only the optical system but also the illumination system gains the benefit of hermetic closure.

In other embodiments, the present inventive concepts contemplate single or compound optical windows affixed by an opaque joint, formed by soldering with gold, its alloys, or similar metals or alloys. A benefit of an opaque joint is to reduce reflections within or between optical elements, increasing contrast and improving image quality.

In other embodiments, the present inventive concepts achieve improved contrast through the use of one or more grooves inscribed into one or more surfaces of an optical element to subdivide it into various regions.

In still other embodiments, the present inventive concepts contemplate a hermetically sealed housing portion formed of dissimilar metals, such as stainless steel, titanium, aluminum, and nitinol. The housing portion may be permanently affixed to the shaft of an endoscope or releasably attached thereto. In certain embodiments, the housing portions contain an imaging system.

In still other embodiments, the present inventive concepts contemplate a handle portion that employs Hall-effect or other electromagnetic switches for controls, eliminating the perforation of the endoscope handle and preserving its hermetic closure.

These and other inventive embodiments are described in more detail in the following detailed descriptions and the figures.

BRIEF DESCRIPTION OF THE DRAWINGS

FIGS. 1 through 16C show representative embodiments according to the principles the present inventive concepts, wherein the same or similar features share common reference numerals in a range of 1-99, which in the case of a similar or analogous feature may be preceded by a numeral in the hundreds range. For clarity, each reference numeral may refer to an item considered generally and abstractly, as well as to instances of the item in the context of one or more embodiments.

FIG. 1A shows a side view of a representative endoscopic system according to the present inventive concepts;

FIG. 1B shows a top view thereof;

FIG. 1C shows a proximal-end view thereof;

FIG. 2A shows a distal-end view of a distal tip of an objective head with a plurality of panes, according to the present inventive concepts;

FIG. 2B shows a longitudinal section thereof, taken along line 2B-2B in FIG. 2A;

FIG. 2C shows a cross-section thereof, with some components removed, taken along line 2C-2C in FIG. 2B;

FIG. 2D shows a distal-end view thereof, with a different cross-sectional line 2E-2E;

FIG. 2E shows another longitudinal section thereof, taken along line 2E-2E in FIG. 2D;

FIGS. 3A and 3B show a side view and corner detail of an exemplary pane for use in an endoscopic system, according to the present inventive concepts;

FIG. 4A shows a distal-end view of the distal tip of an alternative embodiment of an annular (ring-shaped) pane;

FIG. 4B shows a longitudinal section thereof, taken along line 4B-4B in FIG. 4A;

FIG. 4C shows an end view of the light port in isolation;

FIG. 4D is a side view thereof;

FIG. 5A shows an end-view of the distal tip of an alternative embodiment adapted to acquire an image an angle with respect to the longitudinal axis;

FIG. 5B shows a longitudinal section thereof, taken along line 5B-5B in FIG. 5A;

FIG. 6A shows a front view of an alternative embodiment of an optical window or a light port with a half-moon-shaped exposed face;

FIG. 6B is a bottom thereof;

FIG. 6C is a side view thereof;

FIG. 7A shows a front view of a compound window assembly comprising two of the windows of FIG. 6A, gold soldered together;

FIG. 7B is a cross-section thereof, taken along line 7B-7B in FIG. 7A;

FIG. 8A shows a front view of an alternative embodiment of a compound window assembly comprising two of the windows of FIG. 6A with intermediate fused glass frit;

FIG. 8B shows a cross-section thereof, taken along line 8B-8B in FIG. 8A;

FIG. 9A shows a front view of another alternative embodiment of a compound window structure;

FIG. 9B shows a cross-section thereof, taken along line 9B-9B in FIG. 9A;

FIG. 10A shows a side view an alternative embodiment of an optical window with grooves that divide the window into optical regions;

FIG. 10B shows a cross-section thereof, taken along line 10B-10B in FIG. 10A;

FIG. 11A is a longitudinal cutaway view of the proximal handle portion for use in an endoscopic system, such as that of FIG. 1A, according to the present invention;

FIGS. 11B, 11C, and 11D are cross-sections thereof, taken along the lines 11B-11B, 11C-11C, and 11D-11D, respectively, in FIG. 11A;

FIG. 12 is a longitudinal cutaway view of a blank for the handle of FIG. 11A;

FIG. 14 shows a cutaway view of a distal transition element for use with the handle portion of FIG. 13; and FIG. 15 is a cutaway view of the handle housing assembly of for an endoscopic system such as that of FIG. 1A, according to the present inventive concepts.

FIG. 16A shows a side view of an alternative embodiment of a housing portion according to the present inventive concepts.

FIG. 16B shows a front view of the housing portion of FIG. 1A.

FIG. 16C show a rear-view of the housing portion of FIG. 1C.

Figure 12:
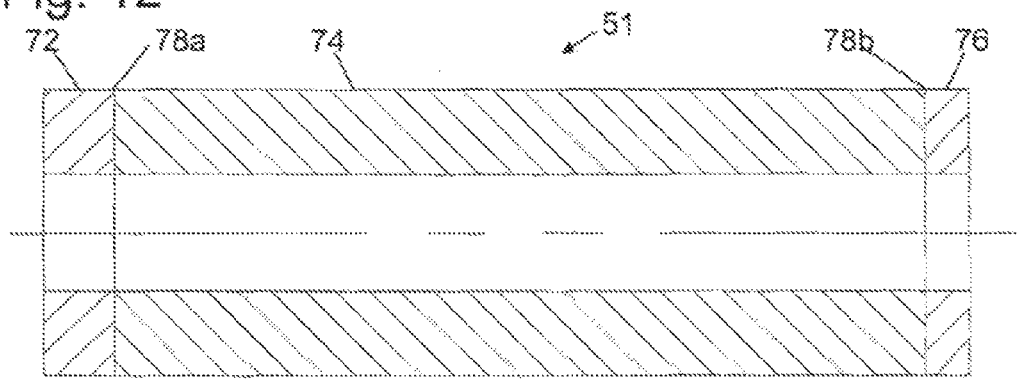
Figure 13A:
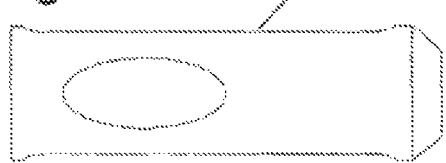
FIG. 13A shows a top view of a handle housing formed from the handle blank of FIG. 12.
Figure 13C:
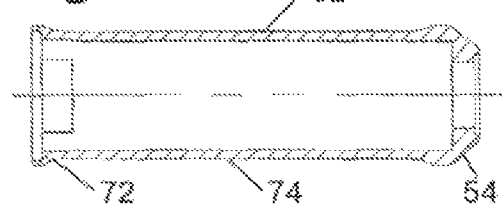
FIG. 13C shows a longitudinal cutaway view thereof, taken along the line 13C-13C in FIG. 13B.
Figure 13B:
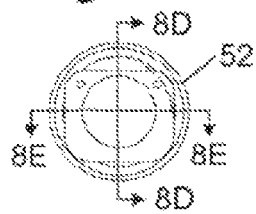
FIG. 13B shows an end view thereof.
Figure 13D:
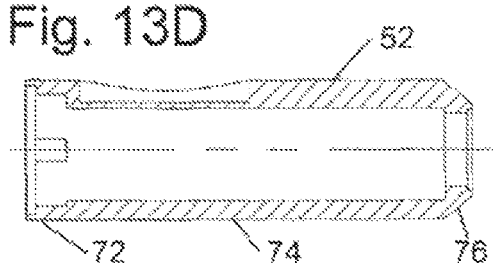
FIG. 13D shows another longitudinal cutaway view thereof, taken along the line 13D-13D in FIG. 13B.

The foregoing is not intended to be an exhaustive list of embodiments and features of the present inventive concepts; persons skilled in the art are capable of appreciating other embodiments and features from the following detailed description in conjunction with the drawings.

DETAILED DESCRIPTION OF THE INVENTIVE CONCEPTS

Definitions

"Hermetic" and its variations herein refer to a sealed, gas-tight, and fluid-tight vessel, tube, or enclosure relative to the environmental conditions under which a housing or enclosure relative to the environmental conditions under which an endoscopic housing or enclosure described herein would normally be subjected.

"Melted-metal seal" and its variations herein refer to any joint formed by any of various soldering, brazing, welding, or fusion techniques such as laser welding, and gold soldering.

"Dissimilar metallic materials" in the context of this application refers to metallic materials that are not directly joinable by welding techniques for forming melted-metal seals, due to melting point or metallurgical incompatibilities in the base metal materials to be joined.

"Gold soldering" herein refers to the use of gold or its alloys as a fusible material to form a joint between base materials. All joints identified as gold soldered indicate that gold or gold-based solder or filler is a preferred welding technique for medical endoscopic systems, because it creates a biocompatible, ductile, chemically inert hermetic closure at a relatively low temperature. It is understood that "gold soldering" herein does not exclude the use of other fusible materials, metals, or alloys, particularly if the fusible material is biocompatible and can withstand repeated autoclave cycles. Soldering with other biocompatible metals or alloys, for example, may replace gold soldering for certain joints.

"Laser welding" herein refers to any of various welding techniques that employ substantially coherent light to generate the heat required to fuse parts together. All joints identified as laser welds indicate that laser welding is a preferred technique because it is clean, accurate, fast, and does not damage sensitive components. It is understood that "laser welding" herein does not necessarily exclude alternative joining techniques such as gold soldering, electronic beam welding, and press fit, however.

"Light" includes both visible and invisible portions of the electromagnetic spectrum, as well as polarized, pulsed, filtered, and coherent (laser) light.

"Pane" or "optical pane" as used herein refers to windows or ports with any transmissive efficiency that allow transmission of some portion of the electromagnetic spectrum for purposes of image acquisition by an imaging system for an endoscope or for illumination of a target site in a patient's body.

"Prism" herein includes a mirror or other optical element for diverting the path of a light ray.

Referring to FIGS. 1A, 1B, and 1C, endoscope 20 comprises a distal end portion 22 including an objective head 28, a shaft 26, and a proximal end portion 24 including a handle portion 50. Referring to FIGS. 2A-2E, objective head 28 includes an electronic imaging system 30 for acquiring an image and an illumination system 32. Imaging system 30 typically includes an optical system 31, and one or more image-capture devices 38, plus supporting electronics, conductors, and connections. As discussed in more detail below optical panes of light transmissive material have a surface on the exterior of the endoscope and are in optical alignment with the imaging system and illumination system. (A "pane" may also be referred to herein as a "window" or "port", or portion of either, depending on function.)

Optical system 31 typically includes one or more panes comprising an optical windows 34 and one or more internal optical elements 33a through 33n. Internal elements 33a through 33n may include lenses, prisms, or mirrors, alone or in any combination. Some embodiments further include a prism 36 adapted to reflect light to image-capture device 38.

Optical window 34 is a port, capable of allowing transmission of electromagnetic energy such as visible light. The port is disposed in the distal tip of objective head 28 to seal or protect imaging system 30 and, optionally, to provide optical effects. Window 34 may be optically coated (for example, to improve light transmission) or colored or patterned (for example, to filter or otherwise modify light entering optical system 31). Window 34 may be a circular cylinder, mounted in the distal tip of objective head 28 with its axis parallel to objective axis 25, exposing a circular face, as shown in FIGS. 2D and 3F. But, any shape that covers the objective element of imaging system 30 is suitable for the purpose. For example, the exposed face may be square, rectangular, linear, polygonal, or irregular.

In certain embodiments, objective head 28 includes a windowed closure for the distal end of shaft 26, such as cap-like, metal cover 40 joined to shaft 26 at weld 42 as discussed below. The distal surface of cover 40 provides an aperture or other receiver for holding each optical window 34, each light port 35, or compound window assembly, as detailed below. In an embodiment, the outer diameter of cover 40 substantially equals that of shaft 26, so that cover 40 abuts shaft 26 and weld 42 is a butt joint. In another embodiment, cover 40 slips over the distal end of shaft 26. Accordingly, the inner diameter of cover 40 approximately equals the outer diameter of shaft 26, so that cover 40 overlaps shaft 26, and weld at a position 42 seals the proximal end of cover 40 against the adjacent inserted surface of shaft 26. In another embodiment, cover 40 slips into the distal end of shaft 26. Accordingly, the outer diameter of cover 40 approximately equals the inner diameter of shaft 26, and weld 42 seals the distal end of shaft 26 against the adjacent inserted surface of cover 40. The phrases "inner diameter" and "outer diameter" herein refer to the nesting sequence of cover 40 and shaft 26 and do not imply that cover 40 and shaft 26 necessarily have a circular cross-sectional profile. The outer profile of the inserted part should generally conform to the inner profile of the surrounding part, facilitating the formation of a hermetic seal at weld 42.

Illumination system 32 is a means of illuminating the site of interest, typically with visible light, but alternatively with any part of the electromagnetic spectrum. Illumination system 32 includes at least one light source 65 (FIGS. 11 and 15), at least one pane comprising light port 35, and, in some embodiments, at least one light conductor 67. Light source 65 may be, for example, one or more solid-state lighting sources (e.g., LEDs), which may be located anywhere inside endoscope 20. Alternatively, light source 65 may be a light conductor such as a fiber-optic bundle coupled to an external light source. Other light-generating devices are within the scope of the present inventive concepts.

Figure 15:
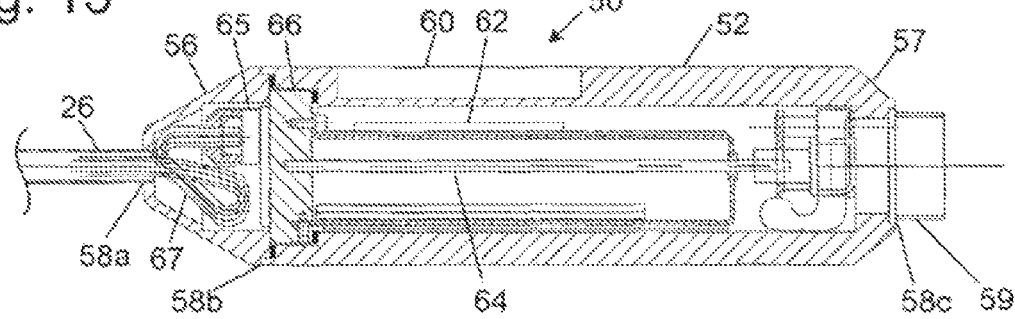

Illumination system 32 may rely on one or more light conductors 67 such as one or more fiber-optic bundles to transmit light from light source 65 to light port 35 and subsequently to the site of interest. For example, as shown in FIG. 15, light source 65, here one or more LEDs in handle 50, generates light transmitted by light conductor 67 through shaft 26 to objective head 28. In an alternative embodiment, one or more light sources 67 may reside within a housing or enclosure, such as the objective head 28 portion of the endoscope shaft, eliminating one or more light conductors 67.

Light port 35 is a pane similar to optical window 34 and set into cover 40 at the distal tip of endoscope 20 to protect at least one illumination system 32 having at least a light source, to alter the characteristics of the transmitted light, or both. Light port 35 may be transparent, translucent, optically coated, or colored to form a filter or to achieve other desired optical effects. For example, light port 35 may have a frosted surface to diffuse light from illumination system 32. Light port 35 may be a circular cylinder as shown in FIGS. 2D and 3F, mounted to expose a circular face. Any shape that creates a cover for at least one illumination system 32 is suitable for the purpose, however. For example, the exposed face may be square, rectangular, linear, polygonal, or irregular. For example, FIGS. 4A-D show a light port 135 with an annular (ring-shaped or washer-shaped) exposed face adapted to cover multiple illumination systems 32 arranged around the periphery of the distal tip of objective head 28, so that "hole" 135b leaves an interior portion of the distal tip uncovered. Although light port 135 and optical window 32 are often discussed herein as physically distinct parts, some embodiments may employ a single physical part for both purposes.

A contemplated material for an optical pane such as window 34, light port 35, or both, is optical sapphire. Transmissive materials other than sapphire may be suitable for the present inventive concept. In certain embodiments, discussed below, the selected material needs to withstand melted-metal assembly techniques and the high-pressure, high-temperature autoclave environment. The choice of optical sapphire reflects its exceptional hardness and toughness, which reduce the risk of scratches and other damage during use, autoclaving, handling, and storage. A filter, coating, or other optical property or treatment may be associated with a window 34 or port 35 to achieve desired effects.

The arrangement and configuration of optical window 34, light ports 35, and objective axis 25 may be implemented in a variety of ways for the purposes of the present inventive concepts. FIGS. 4A and 4B show an embodiment with multiple illumination systems 32 arranged around the perimeter of the distal tip of objective head 28. FIGS. 5A and 5B show an embodiment with the objective axis 25 offset at an angle 39 from the longitudinal axis of objective head 28 via a prism or mirror 37.

Image-capture device (image sensor) 38 may be a Complementary Metal Oxide Semiconductor (CMOS) chip, a Charge Coupled Device (CCD) chip, or other device capable of translating an optical image into a digital or analog signal. Imaging system 30—essentially a miniature video camera—may be a fixed-focus or focusable system. For additional disclosure about imaging systems for endoscopes, see PCT Patent Application number 03/00399, Publication Number WO 03/098913, titled "Miniature Camera Head," filed 15 May 2003, the entire disclosure of which is hereby incorporated by reference in its entirety.

To help endoscope 20 withstand sterilization conditions, melted-metal seals such as solder joints, brazed joints and other metallic fillers; laser-welded joints; or solid-state coalescence joints (e.g., friction-welded joints) may be used to create a hermetically sealed enclosure for delicate or sensitive components. Accordingly, endoscope 20 may be constructed without any exposed O-ring, silicone, or adhesive seals such as epoxy seals. Hospital or clinical staff can place the entire instrument—including its handle 50, shaft 26, objective head 28, and imaging system 30—directly into an autoclave. This straightforward procedure saves time, saves cost, and reduces the risk of patient complications such as iatrogenic infection. The hermetic construction of an endoscope 20 according to the present inventive concepts helps to protect and prevent damage or degradation to sensitive system components during autoclave sterilization.

To achieve these benefits, an endoscope 20 according to certain inventive embodiments employs a combination of sealing technologies as detailed below.

Hermetically Sealing Optical Windows and Light Ports

As discussed above, an electronic endoscope 20 typically includes an electronic imaging system 30 disposed in an enclosure, such as objective head 28, that is insertable into a target site in a patient's body. In the embodiment shown, the distal-most optical element of imaging system 30 is optical window 34, typically a transparent view port mounted on the distal end of cover 40 to protect the internal components of imaging system 30. Each illumination system 32 may have a similar protective light port 35.

One embodiment of the present inventive concepts is the hermetic arrangement of imaging system 30 behind optical window 34, and illumination system 32 behind one or more light ports 35, disposed at the distal end portion of endoscope 20. To achieve a hermetic seal, the attachment method may be a melted-metal seal, such as gold soldering. Similar metals and alloys are within the scope of the present inventive concepts, particularly fusible material that is biocompatible and can withstand repeated autoclave cycles, and can create a soldered or brazed joint.

For example, FIGS. 2A-3G show various views of an embodiment with optical panes in the nature of optical window 34 and light ports 35. These panes may be optical sapphire. In the embodiment shown, each window 34 and port 35 fits into a corresponding receiver at the distal end portion of the endoscope 20. In this example, the receivers are apertures in a cover 40. For medical instruments, a suitable material for the receivers is medical grade stainless steel. A fusible material, such as gold solder 44 is applied to the joint or interface between each window 34 or port 35 and its aperture. Gold solder 44 is applied to the entire perimeter of window 34 or port 35 to achieve a hermetic closure. Gold solder 44 may require an application of gold via metallization, to the perimeter of window 34 or port 35 and to the mating surface of each aperture in cover 40, to create joint surfaces receptive to gold solder 44 or other interface material. Those skilled in the art will appreciate that equivalent melted-metal sealing techniques may require similar treatments to dissimilar joining surfaces in order to achieve a strong bond. These techniques are well-known in the art. See for example, the prior patents cited in the Background section above.

The assembly sequence of cover 40 and windows 34 or ports 35 is an aspect of the present inventive concepts. During assembly of certain embodiments, each window 34, port 35, or compound window structure is soldered into its aperture on the distal surface of cover 40 before cover 40 is welded to the distal end of shaft 26. Creating a melted-metal seal, preferably gold solder, joints 44 on a detached cover 40 permits, for example, the subassembly of cover 40, windows 34, and ports 35 to cool off before being joined to distal end of shaft 26 containing the internal parts of optical system 31 and illumination system 32. Pre-soldering windows 34 and ports 35 into cover 40 eliminates heat transfer during the gold soldering process to the internal parts of optical system 31 and illumination system 32. Pre-soldering therefore eliminates heat damage to the internal parts of objective head 28, which may occur at temperatures of about 150° C. A subsequent laser weld 42 joining cover 40 to shaft 26 does not generate heat that harms optical system 31 or illumination system 32.

A particular benefit to the assembly sequence detailed above is the ability to protect both optical system 31 and illumination system 32 with melted-metal seals. Illumination components such as fiber-optic bundles and LEDs are especially sensitive to heat damage during soldering. Pre-soldering light port 35 to cover 40 specifically permits the replacement of a flexible, semi-flexible, or adhesive seal between port 35 and cover 40 with a melted-metal seal 44. Totally eliminating non-melted-metal seals with respect to optical system 31, illumination system 32, or both, yields an objective head with a durable hermetic enclosure.

Another benefit to the assembly sequence detailed above for an objective head is that the cover/panes subassembly may be joined to the shaft assembly in one step, simplifying final assembly and reducing risks to components inside the shaft during assembly. For example, pre-assembly allows the cover/panes subassembly to be inspected and cleaned before being attached, reducing the risk of trapping flux or other foreign matter inside the assembled objective head. Soldering windows and ports in-place, contrary to the present inventive concepts, requires a more-complex assembly process with a greater potential for error, less potential for intermediate inspection, and closer proximity to delicate parts.

In another embodiment, FIGS. 4A through 4D show an optical window 34 with a circular exposed face and a light port 135 with an annular (ring- or washer-shaped) exposed face. In this embodiment, window 34 is attached to cover 40 by gold solder 44a as described above. Light port 135, in contrast, requires gold solder 44b around the exterior perimeter and gold solder 44c around the interior perimeter of a hole 135b.

Compound Window Construction for Improved Optics

Instead of placing panes into separate openings machined into a distal cover, the present inventive concepts contemplate that the imaging and illumination systems may be placed behind a single, common window unit. However, if the systems are not behind separate panes, undesired diffused or reflected light may enter the imaging system, reducing image contrasts or causing other negative light effects. Therefore present inventive concepts contemplate a single, compound window unit with multiple panes. The multiple panes may be individual components joined together as a single unit or they may be a monolithic, single unit with distinct pane zones. Optical boundaries or interfaces formed between panes advantageously reduce internal reflection and light diffusion.

Contemplated advantages of the various embodiments of compound windows include reduced cost, ease of assembly, and the ability to select and customize each pane 335 according to its particular function and purpose.

For example, FIGS. 6-9 show an optical pane 235 with a half-moon shape. Such shapes may be joined to form compound window structures.

In another example, FIGS. 7A and 7B show panes 335 joined by, for example, gold or similar solder 344, which also provides a boundary between the panes 335 and around their combined perimeter, forming a compound window assembly. Each of the upper and lower panes may function as an optical window, light port, or both.

In another example, FIGS. 8A and 8B show panes 435 separated by an opaque boundary substance 444, such as fused glass frit.

In another embodiment, FIGS. 9A and 9B show a compound window assembly with an optical window 534 set into an aperture cut or formed into light port 535, with the panes joined by a boundary material 544, such as a gold-based solder.

The compound windows described herein may be implemented in a range of sizes and shapes. The compound window shown in FIG. 8A may be dimensioned to provide a minimally invasive endoscope, which would have a diameter slightly larger than that of the window: for example, about a 4.5 mm window diameter, with 0.1 mm to 0.2 mm of opaque interface 444. Similarly, the compound window of FIG. 9A may have about a 4.5 mm outer diameter for the outer pane 535, and the inner pane 534 may have about a 2 mm-2.5 mm diameter, with 0.1 mm to 0.2 mm of opaque interface 544. Those skilled in the art will appreciate that various shapes for optical window 34 and light port 35 obligate corresponding adaptations to cover 40 and to the application of a boundary material such as gold solder.

The use of gold solder for assembly of panes and formation of a boundary in a compound window creates a chemically non-reactive hermetic seal for the compound window.

Sapphire and other hard optical materials are desirable for abrasion and scratch resistance in permanent endoscope sealing windows. These materials are difficult to cut or form. This makes forming a compound window of sapphire challenging. Sapphire, however, can be grooved by chemical or ion etching, abrasive cutting, or laser ablation. With some specific types of glass, such as those used for molded lenses, it may be possible to form grooves through a heating-and-coining operation. The grooves alone reduce the reflected component by dispersing light. The addition of an opaque, absorbing material in the grooves further reduces the reflected component by absorbing some of the dispersed light.

FIGS. 10A and 10B show a pane 635 with a groove 646 cut, incised, etched, or otherwise indented into its first surface and a second groove 648 cut, incised, etched, or otherwise indented into its second, opposing surface. The offsetting of grooves 646 and 648 on opposite sides of the window define pane 635 and produce an effectively deeper and superior optical boundary between a pane for an illumination source and a pane for an imaging system.

Grooving and opaquing in or on a window surface reduces or eliminates light piping within the optical material by introducing light breaks that absorb, disperse, or scatter radiation. This reduces reflective coupling between two parallel surfaces.

In summary, the present invention contemplates compound pane arrangements, where an optical boundary separates panes for an imaging system and an illumination system. The optical boundary may be formed from opaque material defining a boundary, or indented area of a pane to define a boundary, or both. Notably, the term "opaque", as used herein, is a relative term that does not preclude the use of materials that are substantially opaque and significantly, but not necessarily completely, reduce an undesired optical effect. A material may also be wholly or substantially opaque as to selected portions of the electromagnetic spectrum of interest, but not to others that are not of concern.

Melted-Metal Seal Attaching Windowed Closure to Shaft

In the example embodiment shown, endoscope 20 includes a shaft 26 with an imaging system 30 at the distal end portion 22 and a handle portion 50 with controls 60. Shaft 26 is essentially a metal tube or pipe, often, but not necessarily, with a circular cross-sectional profile.

In an advantageous assembly method, a distal end portion of shaft 26 remains open during assembly, for example, to facilitate the insertion and assembly of imaging system 30. To provide a hermetic closure at distal end 22, a windowed closure, such as a cap-like cover 40 may be attached to distal end of shaft 26. A suitable cover 40 has an approximately cylindrical form, closed at its distal end (except for receivers for optical window 34, light ports 35, or both), and open at its proximal end. The opening at the proximal end of cover 40 should be sized and configured to fit the reciprocal open end of shaft 26. For example, if the distal end of shaft 26 has a circular cross-sectional profile of a given outer diameter, then cover 40 should have a proximal end with substantially the same profile and diameter.

An aspect of the present inventive concepts is the use of at least one melted-metal or coalesced metal seal at a position 42 on the shaft assembly. Typically, but not necessarily, a laser weld attaches the open proximal end of metal cover 40 to the open distal end of shaft 26, creating a fused, hermetic closure. Laser welding is a preferred joining technique because it is clean, accurate, fast, and does not typically damage sensitive components. Alternative joining techniques such as gold soldering, electron beam welding, and press fit are within the scope of the present inventive concepts. For example, FIGS. 2B and 2E show longitudinal cutaway views of the distal end of a representative endoscope 20 according to the present inventive concepts. As shown, cover 40 attaches to shaft 26 via a laser weld at a position 42 applied to the joint between cover 40 and shaft 26. Laser weld 42 is applied to the entire joining surfaces of cover 40 and shaft 26.

While laser welding generally is known, in this novel application for a windowed closure, it provides a metal seal resistant to pressure, moisture, and heat and therefore able to withstand the harsh environment within an autoclave.

Handle with Enclosed Controls and Hermetic Connectors

The proximal end portion 24 of endoscope 20 includes a proximal housing portion or handle portion 50 that may contain controls 60, such as buttons and connection points such as hermetic connector 59. The housing or handle may contain other systems or components, as well. Adapting handle 50 to withstand the autoclave environment requires creating a handle housing 52 that provides for hermetically sealing all connections and controls. FIGS. 1A and 1B show an external view of handle 50, and FIGS. 11A and 15 show cutaway views thereof.

In the embodiment shown, handle 50 comprises a handle housing 52, a distal transition element 56, a proximal transition element 57, at least one hermetic connector 59, and zero or more controls 60. It further comprises zero or more switch means that can be activated without creating an opening in a housing, such as handle 52. For example, the switch means may be a Hall-effect or other magnetic, electronic, or wireless switches 62, which advantageously do not require any opening in handle housing 52, furthering the objective of creating a hermetic enclosure.

In certain embodiments, the present inventive concepts contemplate the use of a solid-state welding technique to create a blank 51, formed of dissimilar materials. A housing 52 so constructed advantageously preserves the ability select metals on a part-by-part basis guided by the purpose of the part and the properties of the available metals and alloys. The large aluminum surface area of handle housing 52, for example, beneficially improves its ability to dissipate heat. Housing 52 simultaneously enables the formation of melted-metal seals yielding a hermetic enclosure.

Figure 14:
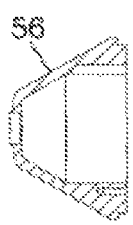

Handle 40 may include a distal transition element 56. The transition element is a transitional cap fabricated from a metal compatible with that of shaft 26, so that transition element 56 may be joined to shaft 26 via melted-metal seal 58a. For example, if shaft 26 is made from a stainless steel, then transition element 56 is made from a compatible stainless steel, facilitating attachment of transition element 56 to shaft 26 via a laser weld 58a. Transition element 56 may be a distinct part fabricated by, for example, stamping, casting, turning, or spinning; or it may be a transitional shape that is machined into the distal end of handle blank 51. Transition element 56 is joined to handle housing 52 via a melted-metal seal. For example, if transition element 56 is made from a stainless steel, then distal end of handle housing 52 is made from a compatible stainless steel, facilitating attachment of transition element 56 to housing 52 via laser weld 58b. FIG. 14 shows a cross-section of transition element 56 in isolation.

Proximal transition element 57 is a transitional cap made from a metal compatible with that of hermetic connector 59, so that transition element 57 may be joined to connector 59 via melted-metal seal 58b. For example, if the body of hermetic connector 59 is made from titanium, then transition element 57 is also made from titanium, facilitating attachment of transition element 57 to connector 59 via laser weld 58b. Transition element 57 may be a distinct part, fabricated by, for example, stamping, casting, turning, or spinning; or it may be a transitional shape machined into the proximal end of handle blank 51 as shown in FIG. 11. It is noted that a transition element is optional. For example, it is contemplated that a shaft may be connected directly to a housing portion, or the shaft may have a transition element or portion.

Hermetic connector 59 is an electrical and electronic connection point adapted to withstand the high-temperature, high-pressure autoclave environment. Connector 59 provides a means for detachably connecting handle 50 and thereby endoscope 20 to (for example) a power supply, devices for displaying, processing, or recording the image, and other external equipment via conductors 54. Connector 59 is preferably joined to handle housing 52 via a melted-metal seal. In an embodiment, the body of connector 59 is made from titanium and joined to housing 52 via laser weld 58c.

A Hall-effect or magnetic switch 62 is a contact-less sensing device that operates by sensing either an external magnet or a ferrous object. The electromagnetic operating principle of a Hall-effect switch is known in the art and beyond the scope of the present disclosure. What is important here is that a Hall-effect switch 62, in conjunction with a control 60, provides a means for controlling endoscope 20 without perforating handle housing 52. Referring to FIG. 15, each Hall-effect switch 62 resides topologically inside the enclosure of handle 50. Each control 60 remains topologically outside the enclosure of handle 50. The communication between each Hall-effect switch 62 and the corresponding control 60 is electromagnetic, not mechanical, thereby preserving the hermetic closure of handle 50.

A control 60 is a push button, toggle switch, or similar device affixed to the outside of handle housing 52 and in electromagnetic communication with a particular Hall-effect switch 62. Each control 60 comprises a magnet or ferrous object adapted to move in response to a predefined user action. The corresponding switch 62 detects the motion of the magnet or ferrous object and responds by issuing a control signal to an electronic component of endoscope 20. The component interprets the signal in a predefined manner in order to enable, disable, or otherwise modify a predefined aspect of the operation of endoscope 20.

For example, suppose control 60 is a button configured as a switch to enable or disable an illumination system 32. Depressing control 60 one time might turn the light source "on," and depressing control 60 a second time might turn the light source "off." To the user, the operation of control 60 seems like that of a common toggle switch connected to illumination system 32. In reality, no mechanical connection exists between the button and illumination system 32. In reality, pressing control 60 one time induces a response in a corresponding Hall-effect switch 62. Conductors within endoscope 20 pass this response, or a derivative of it, to one or more electronic devices within endoscope 20. These devices interpret the response as a predetermined control signal and turn illumination system 32 "on." Pressing control 60 a second time yields a similar chain of events interpreted as a request to turn illumination system 32 "off." The specific benefit of this adaptation is to provide a mechanism for controlling the operation of endoscope 20 without violating the hermetic enclosure of handle 50.

The number of controls 60 (and the corresponding switches 62) depends on the particular purpose of endoscope 20. A typical endoscope 20 has several controls 60. Embodiments with zero, one, or multiple controls 60 are within the scope of the present inventive concepts. An embodiment with zero handle-mounted controls might provide any needed control signals via hermetic connector 62, for example. Alternatively, an endoscopic system may include a remote control that wirelessly communicates with systems or components in an endoscope housing, allowing for a hermetic endoscope.

Enclosure of Dissimilar Materials Formed Using Solid-State Welding

Handle 50 is a sealed enclosure that protects switches 62 and other internal components of endoscope 20 such as printed circuit board 64, light source 65, and heat sink 66. To facilitate insertion of components into handle 50 during manufacture, handle 50 includes a handle housing 52, a distal transition element 56, a proximal transition element 57, and at least one hermetic connector 59. During assembly, these components are joined by seals (interfaces) 58a, 58b, and 58c to form a hermetically sealed enclosure. Distal transition element 56, proximal transition element 57, and hermetic connector 59 may be formed from dissimilar materials. Dissimilar metallic materials may generally be joined using solid-state welding techniques. Solid-state welding is a group of techniques that produces coalescence at temperatures below the melting point of the base materials being joined, without the addition of a filler material. It includes, friction welding, cold welding, diffusion welding, explosion welding, forge welding, hot pressure welding, roll welding, and ultrasonic welding. It is believed that some or all of these techniques may be used to form a hermetic enclosure for a medical instrument, and, in the following description, friction welding is used as a representative technique from the group.

Generally, friction welding involves pressing base metal materials together and frictional engaging the materials relative to each other by, for example, vibration, rotation, or other movement, to generate heat and coalescence of the materials. Friction welding may also be performed by pressing the materials together and frictionally engaging a tool along the boundary of the materials to cause the coalescence. This technique is more particularly known as "friction stir welding".

To facilitate the formation of melted-metal seals, handle housing 52 may be a friction-welded structure as described below.

FIGS. 12 and 13A-13D show one possible construction of handle housing 52. In this embodiment, housing 52 is machined from a friction-welded blank 51. Blank 51 comprises an intermediate section or core 74, a distal cap 72, and a proximal section, such as cap 76. Core 74 may be formed from a metal, such as aluminum, selected for its light weight and heat dissipation. Distal cap 72 may be formed from a metal, such as stainless steel, selected for compatibility with distal transition element 56. Proximal section 76 may be formed from a metal selected for compatibility with hermetic connector 59. Core 74, distal cap 72, and proximal cap 76 may be dissimilar materials not readily joined by conventional melted-metal seal welding, for example. To overcome this dissimilarity, blank 51 may be fabricated by friction welds at positions 78a and 78b. Blank 51 therefore is a kind of laminated structure, with distal cap 72 clad to the distal end of blank 51 at friction weld position 78a, and proximal cap 76 clad to the proximal end of blank 51 at friction weld position 78b. Friction-welding techniques known in the art may be used in this novel construction of an endoscope handle. Blank 51 may subsequently undergo machine operations known in the art to produce the specified form of handle housing 52.

For example, assume that distal transition element 56 is stainless steel and the body of hermetic connector 59 is titanium. Further assume that core 74 is aluminum. In this case, distal cap 72 is joined to the distal end of aluminum core 74 at friction weld 78a, and proximal cap 76 is joined to the proximal end of aluminum core 74 at friction weld 78b. A handle housing 52 derived from this blank 51 is thereby configured to facilitate the formation of melted-metal seals 58b and 58c, such as laser welds. After inserting components into handle housing 51, seals such as laser welds 58b and 58c yield a hermetically sealed enclosure that can withstand autoclave sterilization.

Summarizing, to create a hermetically sealed endoscope 20, all joints from the distal tip 22 to proximal end 24 are formed by melted-metal or coalesced metal seals such as soldering, laser welding, and friction welding. For example, in the embodiment of FIG. 1, the joint sequence, distal to proximal, starts with sapphire optical window 34 and sapphire light ports 35 gold soldered at 44 to apertures in the distal tip of a stainless steel cover 40. Cover 40 is laser-welded at 42 to stainless-steel shaft 26, which is laser-welded at 58a to the distal (apical) end of a stainless-steel distal transition element 56. The proximal (basal) end of distal transition element 56 is laser welded at 58b to stainless-steel cap 72 at the distal end of handle housing 52. Cap 72 joins to aluminum core 74 via friction weld 78a. Core 72 joins to a titanium proximal cap 76 via a friction weld at 78b. Cap 76 is joined to hermetic connector 59 at laser weld 58c. Accordingly, the entire endoscope 20 may be placed in an autoclave for sterilization.

As to controls, the present inventive concepts contemplate the use of one or more Hall-effect or other magnetic switches 62 inside the sealed handle housing 52. Such switches 62 operate by sensing either an external magnet or a ferrous object, contained in, for example, a control button 60 applied to the outside of a sealed handle 50. The use of a control button 60 that relies on a magnet or ferrous object to communicate with a Hall-effect switch 62 creates for handle-mounted control that does not breach the hermetically sealed handle housing 52.

FIGS. 16A-C, show an alternative embodiment of a housing portion 150 for an endoscopic system. In this system, the housing portion encloses a camera assembly that includes an imaging system (not shown). The imaging system may include one or more image sensors. The housing portion includes a mechanical coupling system 790 for releasably coupling the housing portion to an endoscope, typically at the proximal end of the endoscope, at an eye piece. Coupling systems for proximal, camera-endoscope assemblies are well-known in the art and are not detailed here. In one possible embodiment, the imaging system is a 3-chip system. Each chip is dedicated to a specific band of light, typically a primary color. The housing includes optical elements for the imaging system, such as a band separator for separating light into bands, such as the primary colors. An example band separator is a prism, and it is arranged in the housing to deliver each band of light to the chip dedicated to a particular band. The housing portion may also include a set 780 of hermetic connectors, as described above for other embodiments.

The housing portion includes a proximal window 735 that is arranged to optically align with the optical train or elements of a scope and also with the imaging system in the camera housing. The window is set in a front closure 740 for the camera housing, which may include one or more sections. The closure 740 has a receiver for window 735, similar to the arrangement discussed above for a window at the distal end of an endoscope shaft. The window may be sapphire, and the receiver may be defined by a metal fitting or insert 741 included as part of the closure. The window is preferably joined to a metal closure by a melted-metal seal, such as gold soldering 742.

The insert 741 may be joined to a second section 743 in the closure of the same or dissimilar metal as the insert. For example, the second section may be formed of aluminum.

The closure 740 may be joined to a body section 745 made or aluminum or other metals by melted metal seals (e.g., laser welding or solid-state-welding (e.g., friction welding).

Housing portion 150 may also have a rear portion 770 with a connector 771 for electrical coupling with other systems such as video processing and power. This rear connector is generally similar to that in the endoscope embodiments described above. To hermetically seal the housing, the rear portion includes a glass plug 772 formed from molten sapphire, for example. Conductive pins (not shown) hermetically extend from the interior of the housing, through the plug, to the exterior of the housing. The glass plug is formed in a metal insert or fitting 772, which may be fitted in or formed with a flange 773. These parts, if separate pieces, may be stainless steel and laser welded together. The stainless steel insert in turn is set in another section of the housing 776, which may be a dissimilar metal, such as aluminum. As with other embodiments, a solid-state welding technique, such as friction, may be used to join dissimilar materials. The foregoing housing assembly advantageously uses melted materials and melted or coalesced metal seals to provide a hermetically sealed housing for a releasable camera that may be used with new endoscopes or an existing base of conventional endoscopes.

Further details for the construction of a hermetic, releasably-couplable camera assembly are disclosed in co-pending U.S. application Ser. No. 11/109,902, filed Apr. 19, 2005 (provisional 60/563,857 filed Apr. 19, 2004), entitled AUTOCLAVABLE VIDEO CAMERA FOR AN ENDOSCOPE, which is assigned to the assignee of the inventive concepts described herein. The '902 application also discloses hermetic switches, controls, and lens assemblies for a hermetic enclosure. The '902 application is hereby incorporated by reference as if set forth herein in its entirety.

Some or all the present inventive concepts generally may be employed in any kind of endoscope for any kind of medical or industrial application, including rigid endoscopes, capsule endoscopes (e.g., free moving in the gastrointestinal tract), and flexible endoscopes. In addition to traditional constructions of flexible endoscopes, a novel flexible shaft 26 may be fabricated from a super-elastic metal, such as Nitinol or MP35N, configured in spaced flexural lines wholly or partially circumscribing the shaft, similar to accordion-pleats. The operating principle is equivalent to that of the familiar flexible soda straw. Advantageously, a flexible shaft formed from a unibody of metal provides a seamless a hermetic enclosure.

Persons skilled in the art will recognize that many modifications and variations are possible in the details, materials, and arrangements of the parts and actions which have been described and illustrated in order to explain the nature of the inventive concepts and that such modifications and variations do not depart from the spirit and scope of the teachings and claims contained therein.

What we claim:

1. A windowed closure for an objective head for an endoscope, the windowed closure comprising:
    a metal material having at least a receiver for receiving at least one pane for an imaging system and at least one pane for an illumination system comprising a plurality of fiber optic light bundles; and
    a plurality of panes including the at least one pane for the imaging system and the at least one pane for the illumination system disposed in the receiver and joined to the receiver by a melted-metal seal;
    wherein the closure is adapted to connected to an endoscope shaft with the at least one pane for the imaging system in optical alignment with the imaging system and the at least one pane for the illumination system in optical alignment with the illumination system,
    wherein the receiver includes the plurality of panes arranged as a cocentric compound window, the at least one pane for the imaging system is configured to align optically with the imaging system and the at least one pabe for the illumination system is configured to align optically with the illumination system.

2. The closure of claim 1 wherein the closure comprises a cap that complementarily abuts, slides over, or fits within the shaft.

3. The closure of claim 2 wherein the at least one pane of the plurality of panes is joined to the closure via the melted-metal seal comprising gold.

4. The closure of claim 1 wherein an optical boundary is located on the receiver between adjacent edges of the panes for the imaging system and the illumination system to reduce transmission of light across the optical boundary between the panes.

5. The closure of claim 4 wherein the optical boundary comprises an opaque material.

6. The closure of claim 1 wherein the closure comprises stainless steel.

7. The closure of claim 1 wherein a the plurality of panes comprise an optical sapphire.

8. The closure of claim 7 wherein the closure comprises stainless steel and the pane is joined to the closure by the melted-metal seal comprising gold.

9. The closure of claim 7 wherein the sapphire is metallized with gold or a compatible metal before joining.

* * * * *

UNITED STATES PATENT AND TRADEMARK OFFICE
CERTIFICATE OF CORRECTION

PATENT NO. : 8,568,300 B2  
APPLICATION NO. : 12/167901  
DATED : October 29, 2013  
INVENTOR(S) : Novak et al.

Page 1 of 1

It is certified that error appears in the above-identified patent and that said Letters Patent is hereby corrected as shown below:

On the title page item [56]  
References Cited  
U.S. Patent Documents  
insert --5,599,278 02/1997 Hibbard--

In the Claims

Claim 1, Col. 16, Line 40, delete "adapted to connected to an" and insert --adapted to connect to an--

Claim 1, Col. 16, Line 46, delete "as a cocentric compound" and insert --as a concentric compound--

Claim 1, Col. 16, Line 49, delete "pabe for the illumination" and insert --pane for the illumination--

Claim 2, Col. 16, Line 53, insert --endoscope-- before "shaft."

Signed and Sealed this  
Twenty-fourth Day of December, 2013

Margaret A. Focarino  
*Commissioner for Patents of the United States Patent and Trademark Office*